(12) United States Patent
Xian et al.

(10) Patent No.: US 9,453,844 B2
(45) Date of Patent: Sep. 27, 2016

(54) DETECTION OF PROTEIN S-SULFHYDRATION VIA A TAG-SWITCH TECHNIQUE

(71) Applicant: Washington State University, Pullman, WA (US)

(72) Inventors: Ming Xian, Pullman, WA (US); Dehui Zhang, Pullman, WA (US)

(73) Assignee: Washington State University, Pullman, WA (US)

( * ) Notice: Subject to any disclaimer, the term of this patent is extended or adjusted under 35 U.S.C. 154(b) by 197 days.

(21) Appl. No.: 14/507,970

(22) Filed: Oct. 7, 2014

(65) Prior Publication Data

US 2015/0099305 A1   Apr. 9, 2015

Related U.S. Application Data

(60) Provisional application No. 61/887,828, filed on Oct. 7, 2013.

(51) Int. Cl.
*G01N 33/68* (2006.01)

(52) U.S. Cl.
CPC ....... *G01N 33/6815* (2013.01); *G01N 2440/00* (2013.01); *Y10T 436/18* (2015.01); *Y10T 436/182* (2015.01)

(58) Field of Classification Search
CPC ............ G01N 2440/00; G01N 33/68; G01N 33/6815; G01N 21/64; G01N 21/6428; Y10T 436/18; Y10T 436/182; Y10T 436/184
USPC ......... 436/86, 119, 120, 121, 164, 166, 172; 422/82.05, 82.08, 82.09, 430
See application file for complete search history.

(56) References Cited

U.S. PATENT DOCUMENTS

2016/0084845 A1\*   3/2016  Martin ................. G01N 33/582
                                                              435/26

OTHER PUBLICATIONS

Zhang et al. Angewandte Chemie, International Division, vol. 53(2), Nov. 29, 2013, pp. 575-581.\*
Park et al. Methods in Enzymology, vol. 555, 2015, pp. 39-56.\*
Pan et al. ACS Chemical Biology, vol. 8, Apr. 4, 2013, pp. 1110-1116.\*

\* cited by examiner

*Primary Examiner* — Maureen Wallenhorst
(74) *Attorney, Agent, or Firm* — Whitham, Curtis & Cook, P.C.

(57) ABSTRACT

Methods and assays for detecting S-sulfhydration of amino acids in proteins, polypeptides and peptides are provided. The method is a two-step "tag-switch" method employing two reagents consecutively to specifically label, with a detectable label, persulfide (—S—SH) linkages in proteins, polypeptides and peptides.

9 Claims, 1 Drawing Sheet

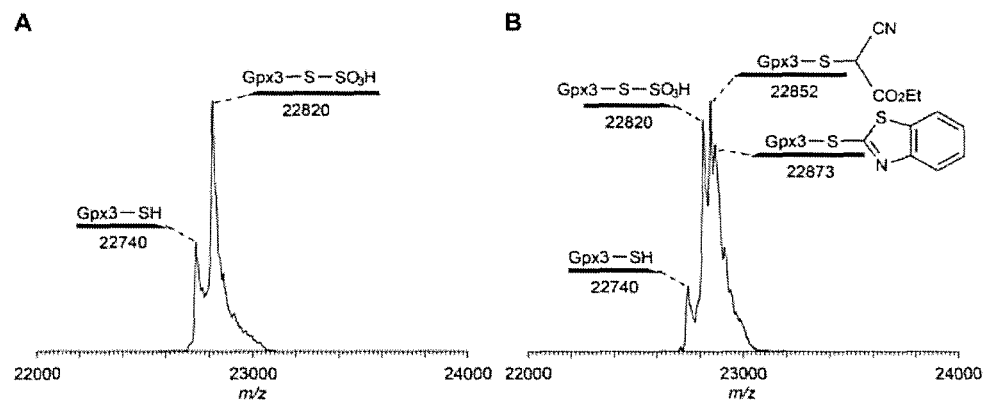
Figure 1 A and B

DETECTION OF PROTEIN S-SULFHYDRATION VIA A TAG-SWITCH TECHNIQUE

CROSS-REFERENCE TO RELATED APPLICATIONS

This application claims benefit of U.S. provisional patent application 61/887,828, filed Oct. 7, 2013, the complete contents of which is hereby incorporated by reference.

STATEMENT OF FEDERALLY SPONSORED RESEARCH AND DEVELOPMENT

This invention was made with government support under R01HL116571 awarded by the National Institutes of Health and CHE0844931 awarded by the National Science Foundation. The government has certain rights in the invention.

DESCRIPTION

Background of the Invention

1. Field of the Invention

The invention generally relates to methods and assays for detecting protein S-sulfhydration. In particular, the invention provides "tag-switch" methods employing novel reagents to specifically and selectively label persulfide (—S—SH) linkages in proteins.

2. Background of the Invention

Hydrogen sulfide ($H_2S$) has been recently classified as a critical cell signaling molecule.[1] Literature published in the past few years increasingly suggests that $H_2S$ is a mediator of many physiological and/or pathological processes.[2] Some of these effects are ascribed to the formation of protein persulfides, or protein S-sulfhydration (i.e. conversion of cysteine residues, —SH, to persulfides, —S—SH). This has been defined as a new oxidative post-translational modification (oxPTM).[3,4] Formation of persulfides is potentially significant because it provides a possible mechanism by which $H_2S$ alters the functions of a wide range of cellular proteins and enzymes.[5] To date, the underlying mechanisms of S-sulfhydration mediated by $H_2S$ are still unclear.[3,4] A significant challenge is that the persulfide group (—S—SH) shows reactivity akin to other sulfur species, especially thiols (—SH), which causes difficulties in developing selective detection methods for S-sulfhydration.[4]

So far two methods have been utilized in the detection of S-sulfhydration (Scheme 1). The first method is a modified biotin switch technique.[5a] It employs an alkylating agent S-methyl methanethiosulfonate (MMTS) to differentiate thiols and persulfides. Thiols (—SH) in proteins are first blocked by MMTS. Persulfides (—S—SH) are believed to remain unreacted and be available for subsequent conjugation to biotin-HPDP. Using this method, a large number of proteins were identified as targets for S-sulfhydration and the basal sulfhydration level of some proteins was estimated to be as high as 25%. In method 2,[5c] it is suggested that both —SH and —SSH can be blocked by alkylating reagents like iodoacetic acid (IAA). Then the persulfide adducts can be reduced by dithiothreitol (DTT) to form free —SH, and subsequently labelled with iodoacetamide-linked biotin (IAP).

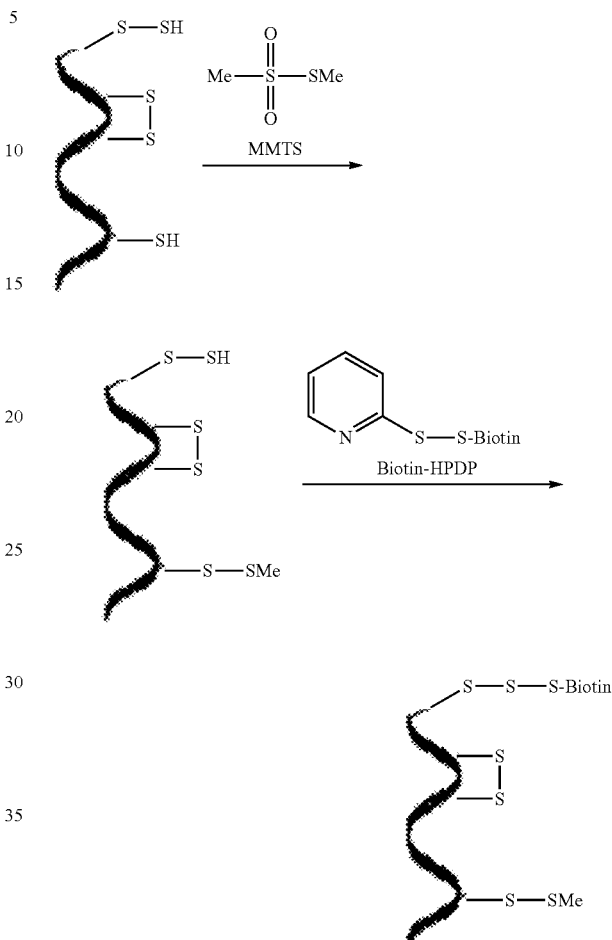

Scheme 1. Current strategies for profiling protein S-sulfhydration

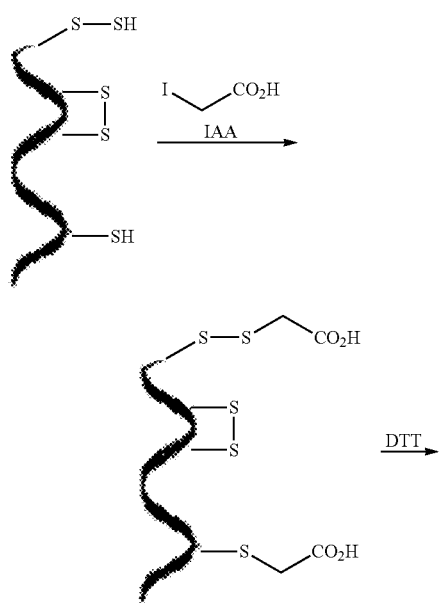

-continued

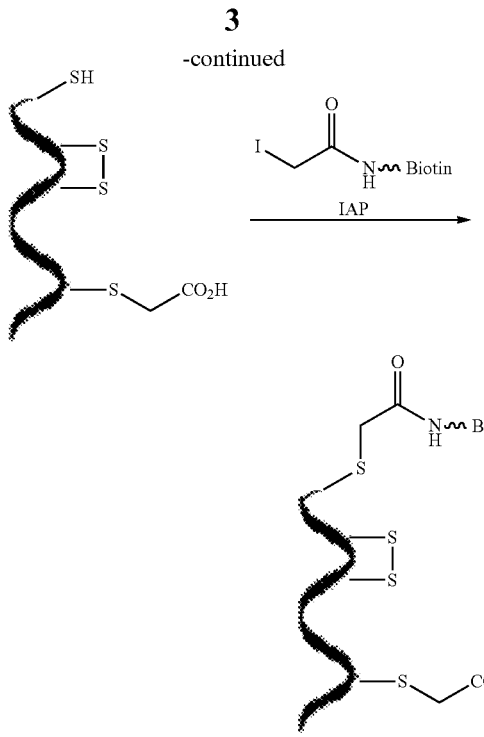

From a chemistry perspective, both methods are problematic. In method 1, the underlying mechanism of selectivity of MMTS for thiol vs persulfide is unclear. Studies have demonstrated that persulfides and thiols should have similar reactivity towards electrophiles such as MMTS.[4] In method 2, it is unclear how DTT reduction would distinguish persulfide modifications from other DTT-reducible residues, such as disulfides and S-nitrosothiols. Therefore, the chemical foundations of current methods are questionable, which may lead to erroneous results. More reliable methods for the detection of protein S-sulfhydration are needed.

SUMMARY OF THE INVENTION

In view of the very similar reactivity of both thiols and persulfides described above, a novel "tag-switch" technique has been developed to specifically detect S-sulfhydration of cysteine residues in proteins, polypeptides and peptides in samples of interest.

As illustrated in Scheme 2, according to the invention, S-sulfhydration in proteins is selectively detected by a two step "tag-switch" method that selectively labels persulfides with reporting molecules (R). Each step of the method utilizes a different reagent. In the first step, a sample of interest comprising one or more proteins of interest is exposed to a first reagent that blocks all SH groups (an "SH blocking reagent"). The first reagent forms a chemical bond with both —SH and —S—SH groups in the proteins to form thioether and persulfide-derived disulfides, respectively, thereby forming "tagged" intermediates (T in Scheme 2 below). When an appropriate SH blocking reagent (BR) is used in this first step, the persulfide-derived disulfide adducts that are created exhibit greater reactivity to certain nucleophiles, compared to the reactivity of the thioethers (or to untagged disulfide linkages). Therefore, in a second step, tagged intermediates are contacted with a second reagent that contains this type of selectively-reactive nucleophile, and the nucleophile reacts preferentially with persulfide-derived disulfides rather than with thioethers (or with other existing sulfides or disulfide bonds). The nucleophile reacts by essentially displacing (replacing) the SH blocking reagent that was attached to S—SH groups in the first step. Thus, the original tagging agent is "switched" in the second step, but only for tagged persulfide adducts. A labelling moiety is generally attached to the nucleophile and becomes associated (indirectly) with each nucleophile-modified persulfide adduct, making it possible to detect the presence of amino acid residues that contained an —S—SH bond in the original sample, i.e. to detect S-sulfhydration of cysteine residues of proteins, polypeptides and peptides in the sample. The specificity of the nucleophile-persulfide adduct interaction insures that the results are not complicated by contaminating signal from other types of sulfur-containing groups.

Scheme 2. Proposed tag-switch technique for S-sulfhydration

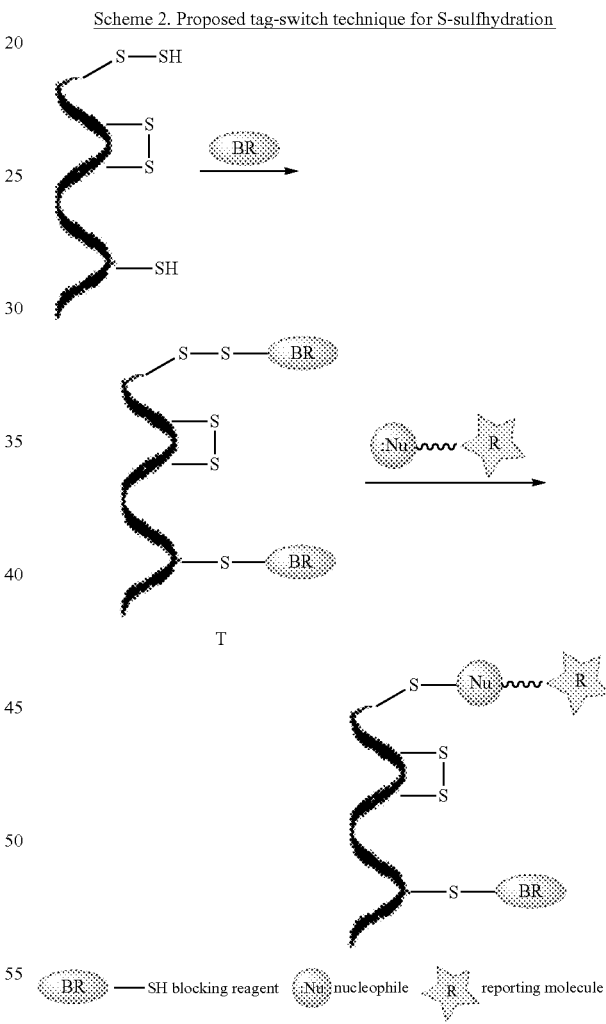

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide methods of selectively detecting S-sulfhydration of cysteine residues in a protein, polypeptide or peptide. The methods comprise a first steps of i) exposing the protein, polypeptide or peptide to a first reagent that forms a covalent bond with —SH and —SSH groups, thereby forming disulfide adducts with both the —SH and —SSH groups; and then a second step of ii) exposing the protein, polypeptide or peptide to a second reagent comprising a nucleophile that selectively reacts with disulfide adducts formed from the persulfide (—SSH) groups. The second reagent also comprises a reporting molecule that is linked to the nucleophile via a linking molecule; and then a third step of iii) detecting (or attempting to detect) the reporting molecule. If the reporting molecule is detected i.e. if "positive detection" of the reporting molecule occurs, this indicates that the cysteine residues of the protein, polypeptide or peptide were S-sulfhydrated. Conversely, if the reporting molecule is not detected (i.e. a negative result is obtained), this indicates that cysteine residues of the protein, polypeptide or peptide were not S-sulfhydrated, or that cysteine residues were not present in the protein, polypeptide or peptide. The method may also include, prior to the step of exposing the protein, polypeptide or peptide to the first reagent, a step of detecting whether or not cysteine residues are present in the protein, polypeptide or peptide. In some aspects, the assay is carried out on a mixture of proteins, polypeptides or peptides, or on a sample containing one or more proteins, polypeptides or peptides. The nucleophile does not react with thioethers or disulfide bonds in proteins, polypeptides or peptides.

Exemplary first reagents, nucleophiles, reporting molecules and linking molecules are described below. In some aspects, one or both of the first and second reagents, typically the second reagent, is associated with (e.g. immobilized on) a solid support material, a resin, a dendrimer or a nanoparticle.

The invention also provides kits comprising a first reagent that forms a covalent bond with —SH and —SSH groups, thereby forming disulfide adducts; and a second reagent comprising a nucleophile that selectively reacts with disulfide adducts formed from persulfide groups. The second reagent comprises a reporting molecule linked to the nucleophile via a linking molecule. Typically, the second reagent is immobilized on a substrate.

BRIEF DESCRIPTION OF THE DRAWINGS

FIGS. 1A and B. Mass analysis of tag-switch assay with Gpx3-persulfide. A) The control reaction between Gpx3 persulfide and ethyl cyanoacetate (without MSBT-A). B) The reaction between Gpx3 persulfide and ethyl cyanoacetate (with MSBT-A).

DETAILED DESCRIPTION

The invention provides methods and kits for selective detection of S-sulfhydration of proteins, polypeptides and peptides in two steps. The method is referred to as a "tag-switch" method because in the first step, S-sulfhydrated (persulfide) groups in a sample are exposed to and chemically react with a first reagent, forming "tagged" persulfide-derived disulfide adducts. However, other sulphur-containing groups in the sample may also react with the first reagent and are thus also tagged, e.g. free sulfhydryl (—SH) groups also chemically react with the first reagent to form thioethers. Other sulphur-containing groups, e.g. disulfides (—S—S—) generally do not react with the first reagent and are not tagged in this step.

The next step of the method is designed to distinguish between tagged persulfide-derived disulfide adducts and tagged thioethers that were formed in the first step of the method. In the second step, the sample is exposed to a second reagent that reacts preferentially with persulfide-derived disulphide adducts, but not with thioethers. The second reagent is generally a nucleophile that attacks and breaks the S—S bond of persulfide-derived disulfide adducts, displacing the first "tagging" reagent (and one sulfur atom of the persulfide-derived disulfides, see Scheme 2). The second reagent also generally comprises a detectable label so that the resulting complex (comprised of the nucleophile attached to the remaining sulphur atom of the original persulfide group and the label, see Scheme 2) can be detected using a suitable detection method. Since thioethers and other sulphur containing groups (e.g. disulfides) do not react with the nucleophile of the second label-containing reagent, they are not labelled and are not detected in the detecting step.

DEFINITIONS

Selective reactivity or selective reaction refers to a chemical reaction that proceeds at a significantly and measurably faster rate and/or which has a significantly and measurably greater equilibrium distribution of product for a reaction of interest, compared to another reaction of interest. As used herein, the nucleophile that is used in the second step of the method is selectively reactive toward the —S—S— bonds in persulfide-derived disulphide adducts when compared to its reactivity toward thioethers, disulfides, or other sulfur-containing groups. Generally, the difference in reactivity is at least about 2-fold, and may be greater, e.g. 5, 10, 15, 20, 25, 30, 35, 40, 45, 50, 55, 60, 65, 70, 75, 80, 85, 90, 95, or 100 fold greater, e.g. 200, 250, 300, 350, 400, 450, 500, 550, 600, 650, 700, 750, 800, 850, 900, 950 or 1000 fold greater, or even more. In some aspects, the reaction may be specific, i.e. the nucleophile that is employed in the second step of the method reacts with persulfide-derived disulfides but does not react at all (or at least not to a measurable, detectable extent) with thioethers, disulfides, or other sulfur-containing groups, i.e. sulfur-containing groups other than persulfides are substantially inert toward the nucleophile.

Protein(s) refers to an amino acid chain with at least about 10 amino acids, and as used herein, includes, for example, terms used in the art such as peptides, polypeptides, and proteins, including modified forms thereof, including pre- and post-translationally modified forms. "Protein", "polypeptide" and "peptide" may be used interchangeably herein, and the method may be used to detect S-sulfhydration of any of these.

Nucleophile refers to a chemical species that donates an electron pair to an electrophile to form a chemical bond in relation to a reaction.

The assay and components thereof are described in detail below.

Assay Components

The First Reagent

The first reagent used in the method is a thiol-blocking "tagging" reagent. This reagent reacts rapidly with both thiol (—SH) and persulfide (—SSH) groups to form blocked disulfide adducts. The adducts generated from persulfides are activated disulfides that preferentially react with nucleophiles, while the adducts generated from thiol groups (e.g. thioethers) are not activated. To meet these criteria, appropriate heterocycle-based thiol blocking reagents are selected and used as the first reagent.

An exemplary generic structure of a thiol blocking "first" reagent is shown in Formula I:

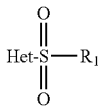

Formula I where Het is a heterocycle, examples of which are provided below; and R1=—CR, —OR, —SR, or —NR, where R=an aryl or alkyl group. Exemplary aryl groups include but are not limited to: phenyl, naphthyl, indenyl, phenanthryl, biphenyl, tolyl, xylyl, furanyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. which may be unsubstituted or substituted with one or more heteroatoms (e.g. N, S, O, etc.); and exemplary alkyl groups include but are not limited to those with from about 2 to about 20 carbon atoms such as methyl, ethyl, n-propyl, or isopropyl, butyl, pentyl, 2-methylbutyl, 2-ethylpropyl, 3-methylpentyl, and the like, as well as cycloalkyls with three or more carbon atoms, and alkenyl groups (alkyls of about 2 to about 20 carbon atoms with at least one carbon-carbon double bond), etc. all of which may be unsubstituted or substituted with one or more heteroatoms (e.g. N, S, O, Cl, F, etc.).

Another exemplary generic structure of a thiol blocking "first" reagent is shown in Formula II:

Formula II where Het is a heterocycle or heteroaryl, examples of which are provided below; and R2 is, for example, —F, —Cl, —Br, —I or —$N_2^+$.

Exemplary heterocycles that are used in the first reagent include but are not limited to:
various nitrogen (or sulfur or oxygen) containing heterocyclic compounds with mono-aromatic rings such as

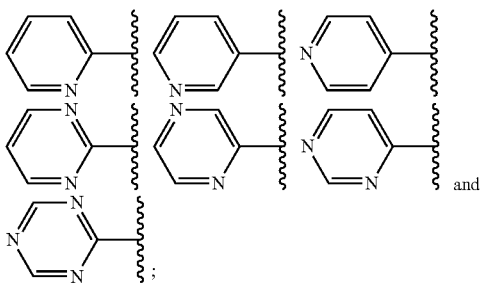

and various nitrogen (or sulfur or oxygen) containing heterocyclic compounds with multiple-aromatic rings such as:

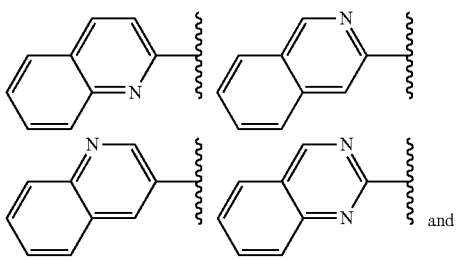

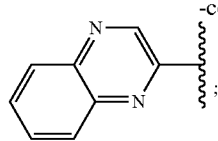

as well as with various aromatic compounds with electron withdrawing groups (such as —$NO_2$) and substituted aryl or heteroaryl groups such as

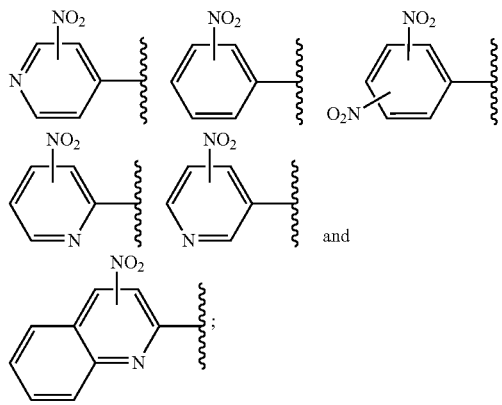

and various other heterocycles such as

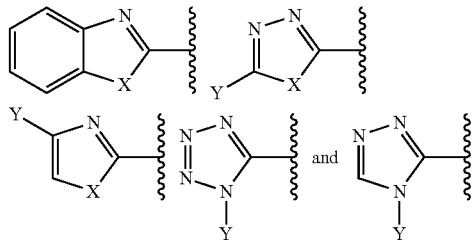

where X is O, S or NH and Y=an aryl or alkyl group such as those listed above for R, and wherein when X and Y occur in the same molecule they are independently selected and so may be the same or different.

The Second Reagent

The second reagent that is used in the assay reacts selectively with the activated disulfide adducts that are generated from persulfides in the first step of the assay, to form final labeled products. In general, this reagent contains a carbon-based nucleophile that is joined to a detectable reporting molecule (label) via a suitable linker. The nucleophile is able to effectively react with activated disulfides (the persulfide-derived disulfide adducts formed in step 1), but either do not react with or do not react as effectively with other disulfides or thiol-derivatives such as thioethers and S-nitrosothiols. A nucleophile species that is suitable for use in the present method has the following general characteristics: a carbon atom connected directly (or through conjugation) with one (or two, or three) electron withdrawing groups. For example, moieties such as carbonyls, cyanos, etc. that are spaced apart in a molecule by three, two or fewer carbon atoms, e.g. that are, in a contiguous chain of atoms that are covalently bonded to each other, separated by the bonds between three, two or fewer carbon atoms along the length of the chain. A generic structure of the second reagent is depicted below:

Exemplary nucleophiles that may be used in the second reagent include but are not limited to:

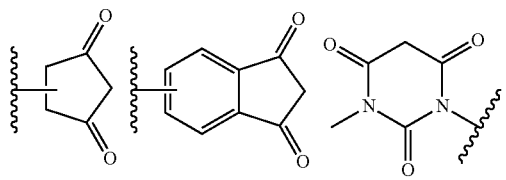

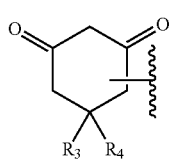

where R3 and R4 are an aryl group and an alkyl group, respectively, such as those listed above for R; and where R3 and R4 are independently selected and so may be the same or different;

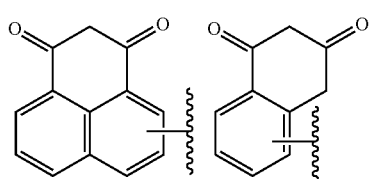

where R5 and R6 are independently selected from: an aryl group or an alkyl group selected from those listed above for R; or are —NR or OR where R=an aryl group or an alkyl group selected from those listed above for R, and

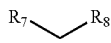

where R7 and R8 are independently selected from —NO$_2$, —CN, —SO$_2$R, —COOR or CONR, where R=an aryl group or an alkyl group selected from those listed above for R.

The second reagent typically includes at least one linking group which joins or tethers the nucleophile to the reporting molecule. Linkers that may be employed in the second reagent generally include carbon chains with from about 2 to about 40 carbons, and which usually contain one or more heteroatoms, and/or aryl groups and/or alkyl groups.

Exemplary linking molecules include but are not limited to:

L1
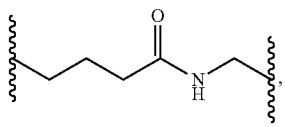

L2
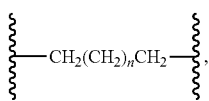

where n = 0 to 40

L3
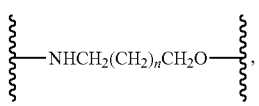

where n = 0 to 40

L4
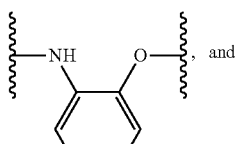
, and

L5
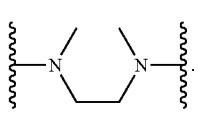

While not specifically shown above, it should be recognized that the linking moiety may be substituted with halogens, cyano, amino, or other groups.

The reporting molecule (label, signaling moiety) that is attached to the nucleophile and used for visualizing and analyzing the assay results may be any reporting molecule that is commonly used for protein analysis. Exemplary labeling entities include but are not limited to: biotin, various fluorescent dyes (coumarin, fluorescein), boron-dipyrromethene (BODIPY), 1,8-naphthalimide), etc; various dansyl-based dyes, various nitrobenzofurazan-based dyes, rhodamine, cyanine dyes, pyrene succinimidyl esters, various pyridyloxazole derivatives, etc., as well as derivatives of these dyes.

The second reagent that is employed is immobilized via association with (e.g. chemical attachment to or incorporation into) a carrier that is immobilized on a substrate. Exemplary substrates include but are not limited to e.g. the surface of a reaction vessel (such as inside the wells of a multi-well assay plant), on a slide, inside tubing or channels designed so that samples low through or over the immobilized carrier, etc. In this aspect, the carrier may be, for example, a solid support material, a resin, a dendrimer, a nanoparticle, etc. Attachment to the immobilized carrier may be via the labeling moiety, or via the linker, or even via the nucleophile, as long as the reaction of the nucleophile with persulfide linkages in the sample is not prevented or attenuated by the geometry of the attachment.

Scheme 3 shows a schematic illustration of an exemplary aspect of the invention. In this example, the first reagent is methylsulfonyl benzothiazole (MSBT) as shown below, where R=alkyl, aryl, —OR, —NR$_1$R$_2$, or —SR (R, R$_1$, R$_2$ can be alkyl or aryl), and the second reagent is biotin-conjugated cyanoacetate (CN-biotin) as shown below.

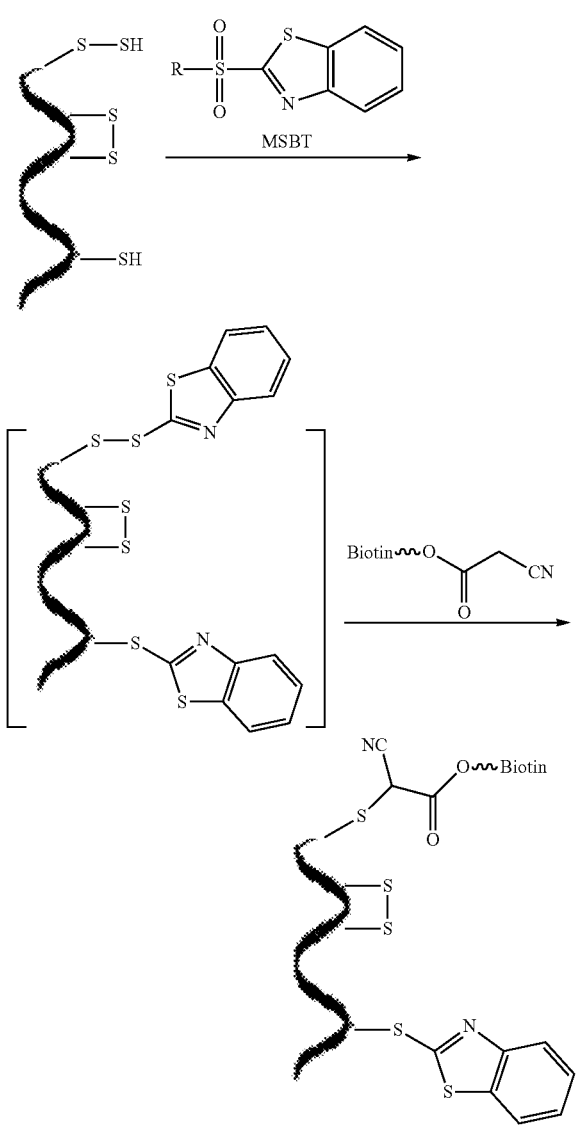

The Assay Method

The method of the invention is generally carried out in vitro by obtaining a sample of interest and testing the sample, with or without processing the sample prior to testing. Samples that may be analyzed using the methods, reagents and kits of the invention include any sample of interest that is suspected of or that may possibly contain molecules containing one or more S-sulfhydryl moieties. In some aspects, the molecules are proteins, polypeptides or peptides, but the invention is not restricted to the detection of S-sulfhydrated chemical groups in such molecules. Given the interest in elucidating cell signaling mechanisms, the sample is often a biological sample. Any type of biological sample may be assessed by the present methods, including samples of cells and/or tissue from prokaryotic bacteria and eukaryotic organisms, including mammals such as humans. The sample may contain cells or tissue (or blood), or may be derived from one or more cells or tissues that has/have been treated, e.g. to remove or isolate non-proteinaceous or other material that is not of interest, and/or to obtain a fraction containing or enriched for one or more components of interest such as proteins, polypeptides and/or peptides. The method is also used for in situ labeling of proteins in methanol- or paraformaldehyde-fixed cells or tissue samples.

Typically, the sample and molecules of interest in the sample are exposed to the first reagent in a reaction vessel or container under conditions that allow the first reagent to react with and modify (form a chemical, usually covalent, bond with) both —SH and —S—SH groups in the sample. Such conditions include carrying out the reaction at a temperature in the range of from about −20 to about 100° C. for a period of time ranging from about 5 min to about 24 hours. The concentration of first reagent that is used may vary according to the sample and other factors (e.g. the reactivity and/or stability of the reagent, the particular molecules and linkages being modified, etc.) but is generally in the range of from about 10 uM to about 100 mM. This first step of exposing is generally carried out by mixing the reagent with the sample, e.g. by pipetting or otherwise placing the reagent into the sample and then agitating the mixture. The first reagent may be immobilized and/or molecules of interest in the sample may be immobilized to facilitate removal of excess reagent prior to conducting the next step of the method. If the reagent is immobilized, then chemical coupling of the immobilized first reagent to —SH and —S—SH groups in the sample "captures" molecules in the sample that contain these groups, attaching them to the immobilized first reagent and sequestering them in the reaction vessel. Excess sample and unreacted reagent may be removed (e.g. by washing) from the reaction container when the reaction is complete, or has proceeded for a period of time sufficient to insure or allow an accurate result to be obtained. If the molecules of interest are immobilized, then excess reagent may be removed by washing. Other means of separating sample molecules from unreacted first reagent may also be used (e.g. centrifugation, antibodies, chromatography, etc.) Alternatively, if the first reagent does not interfere with the reactions of the second reagent, it may be left in the reaction mixture.

The second step of exposing is generally carried out by mixing the second reagent with the reacted sample (already reacted with the first reagent), e.g. by pipetting or otherwise placing the second reagent into contact with the sample and then agitating the mixture. Such conditions include carrying out the reaction at a temperature in the range of from about −20 to about 100° C. for a period of time ranging from about 5 min to about 24 h. The concentration of second reagent that is used may vary according to the sample and other factors (e.g. the reactivity and/or stability of the reagent, etc.) but is generally in the range of from about 10 uM to about 100 mM. In some aspects, the second reagent is immobilized and the reaction takes place as the reacted sample is mixed with or allowed to flow over immobilized second reagent. The second reagent may be immobilized via the labeling moiety, via the linker, or via the nucleophile, as long as the geometry of the immobilization does not preclude or attenuate the ability of the second reagent to interact with and form a chemical bond with persulfide groups in the sample. In this aspect, chemical coupling of the nucleophilic portions of the immobilized second reagent to persulfide groups in the sample "captures" molecules in the sample that contain persulfide groups, attaching them to the immobilized second reagent and sequestering them in the reaction vessel, and unreacted second reagent may be removed from the reaction mix by known methods (e.g. those used for removing unreacted first reagent). Alternatively, if the first reagent or the sample molecules were immobilized, then immobilized persulfide-containing molecules form in the first step react with mobile second reagent and capture it, and excess second reagent is removed e.g. by washing. Alternatively, if the second reagent does not interfere with detection of the final product, it may be left in the reaction mixture.

Alternatively, other agents specific for reacting with any of the components of the assay, (e.g. antibodies specific for reacting with the first reagent, the second reagent or a portion thereof e.g. linker or label, or the molecule of interest) may be used to sequester and/or remove (segregate, partition) the final product from other reactants, as long as the composition that is finally retained for analysis comprises molecules of interest that are chemically bonded to second reagent that has an attached detectable label.

Analysis of the results of the method is performed by detecting the presence of the detectable label in the final reaction product using a technique that is suitable for the particular label that is used. Prior to detection, the sample may or may not be further processed to enrich the sample for tagged and switched molecules, e.g. by chromatography, by anybody capture, by centrifugation, or by any other suitable technique. Detection techniques that are then applied to detect (e.g. to visualize) the final product include but are not limited to: mass spectrometry (MS), electrospray ionization time-of-flight mass spectrometry (ESI TOF MS), Western blot (e.g. SDS-PAGE, transfer to nitrocellulose membrane and identification by anti-biotin HRP-conjugated antibodies), or by affinity or size exclusion chromatography, or by fluorescence detection, e.g. using a fluorescent plate reader (microplate reader) adapted for detecting signals from microtiter plates, or by dot blots, etc. Generally, the amount of label is quantitated by measuring the signal produced by labeled molecules, and serves as an indicator (i.e. correlates with) the amount or level of persulfide linkages that were present in the original sample. In order to quantitate the amount of signal, the signal from suitable positive and/or negative controls is also generally detected, e.g. the amount of signal from one or more analogous molecules (e.g. proteins, polypeptides, or peptides) with a known amount of persulfide linkages (positive control) and the amount of signal from a sample that is known not to contain persulfide linkages. Detection of a statistically significant amount of signal from the experimental sample under investigation indicates that the original sample contained —S—SH linkages whereas the lack of a statistically significant signal indicates that the original sample did not contain such linkages. Those of skill in the art are familiar with the generation of e.g. standard curves using multiple dilutions of control samples and comparing experimental results to control data to quantitate the amount of a substance of interest in an unknown, experimental sample, e.g. by converting measured units (for example, fluorescence units) to units of interest (e.g. an amount or number or concentration of persulfide linkages). The results may be expressed, e.g. as a quantity, a ratio, a percentage, or as some other numerical amount.

The method also encompasses the identification of particular individual proteins, polypeptides, peptides or amino acid residues that are S-sulfhydrated in the original sample, e.g. by molecular weight comparisons, or by isolating and sequencing species of interest that are identified, or by other means known in the art.

The methods of the invention are used to identify S-sulfhydration of proteins, polypeptides or peptides in samples of interest for a variety of applications, e.g. to determine the presence and/or relative distribution of S-sulfhydration in proteins, in cells, in subcellular organelles, in particular pathways in cells, in tissues, blood, or other biological samples, etc. An important application of the technology is to elucidate the occurrence of S-sulfhydration and/or abnormal cell signaling, e.g. associated with or characteristic of disease conditions. As such, the method may be used to detect or confirm the presence of patterns of S-sulfhydration that are associated with particular diseases/conditions, e.g. to diagnose or confirm a diagnosis, or to monitor treatment regimens, or to monitor the progression of a disease/condition, etc.

Kits for carrying out the methods are also provided. The kits include, for example, one or more first and second reagents, one or more control standards (e.g. a protein sample that is known to contain persulfide linkages, or materials for generating such a standard, and/or a protein sample that is known to not contain persulfide linkages), various buffers, and instructions for use. In some aspects, the first and second reagents are conjugated into other commonly used isolation/detection materials (such as solid support, biotin, fluorescent dyes, etc.). The first or second reagent, usually the second reagent, may be immobilized on a suitable substrate, e.g. on beads, a chip, an assay strip or on a surface of a multiwall plate or other reaction vessel. The kits are used, for example, in western blot or high-throughput screening to identify S-sulfhydrated proteins.

EXAMPLES

Example 1

Protein S-sulfhydration (forming —S—SH adducts from cysteine residues) is a newly defined oxidative post-translational modification and plays an important role in $H_2S$ mediated signaling pathways. This study reports the first selective, 'tag-switch' method which can directly label protein S-sulfhydrated residues to stable thioether conjugates. Furthermore it is demonstrated that $H_2S$ alone cannot lead to S-sulfhydration and that the two possible physiological mechanisms include reaction with protein sulfenic acids (P—SOH) or the involvement of metal centers which would facilitate the oxidation of $H_2S$ to HS..

A major challenge in this technology is whether the newly generated disulfide linkage from persulfide moieties display a unique reactivity for a suitable nucleophile to an extent that distinguishes them from common disulfides. SH blocking reagents are well known.[6] However, those capable of fulfilling the criteria for this assay are limited. For example, irreversible thiol-blocking reagents such as maleimides and iodoacetamides display good selectivity and fast reactivity for thiols.[6] However, if such reagents react with persulfides, alkyl disulfide adducts will be produced and the reactivity of the alkyl disulfide adducts would not differ from that of cysteine or glutathionylated protein disulfides. Therefore, these reagents are not suitable for use in tag-switch methods.

We envisioned that a reagent which, upon reaction with persulfides, yielded a mixed aromatic disulfide linkage, might exert the desired reactivity criteria. One potential candidate is methylsulfonyl benzothiazole (MSBT), a recently developed thiol-blocking reagent.[7] Disulfides generated from reaction between MSBT and persulfides might be highly activated and exert a unique reactivity with certain nucleophiles, in particular, enolates.[8]

To test this hypothesis, the reaction between MSBT and persulfide substrates was tested. Since MSBT is a very effective SH blocking reagent[7] and persulfides (—S—SH) are known to have reactivity that is very similar to that of thiols,[4] it was theorized that MSBT would effectively block persulfides. However, it is known that small molecule persulfides are very unstable species[9] so purified/isolated persulfides could not be used in the experiments. Instead, several alternative approaches to in situ persulfide generation from precursors like 1 (Scheme S1 in Materials and Methods below) were attempted and the persulfide intermediates were used directly in MSBT blocking. Results showed that the desired product 3 was obtained, although in low yield (13%). This result demonstrated that MSBT reacts with persulfides to form R—S—S-BT adducts. The major product in the reaction was found to be polysulfides derived from persulfide 2. However, this should not be a concern for the detection of protein persulfides because polysulfide formation is not expected to occur easily on protein persulfides.

TABLE 1

Screening nucleophiles for the tag-switch step

| entry | nucleophile | product (% yield) |
|---|---|---|
| 1 | 1,3-cyclopentanedione | 5a (trace) |
| 2 | 5,5-dimethyl-1,3-cyclohexanedione (dimedone) | 5b (85%) |
| 3 | methyl acetoacetate | 5c (trace) |
| 4 | NC-CH2-C(O)NHBn | 5d (trace) |
| 5 | malononitrile (NC-CH2-CN) | 5e (60%) |
| 6 | methyl cyanoacetate (NC-CH2-CO2Me) | 5f (98%) |

Next, a cysteine substrate 4 was used to screen appropriate nucleophiles for the tag-switch step (Table 1). The preparation of 4 is shown in Scheme S2 in Materials and Methods, below. It should be noted that R—S—S-BT products like 4 are quite stable. They do not react with potential nucleophilic groups such as —OH and —NH$_2$ (Scheme S3 in Materials and Methods). A series of carbon-based nucleophiles were screened as potential candidates. As shown in Table 1, three reagents (dimedone, malononitrile, and methyl cyanoacetate) proved to be effective and the corresponding products 5b, 5e, and 5f were obtained in valuable yields. The reactions were also found to be fast (completed within 20 min). Among these candidates, methyl cyanoacetate (MCA, entry 6) was particularly attractive as the ester group allows easy attachment of reporting molecules. Therefore MCA was selected for the next studies.

Scheme 3. Scope of the reaction of MCA with R—S—S—BT derivatives

R—S—S-BT → 6a-6f

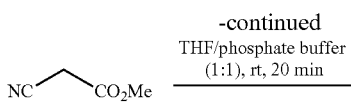
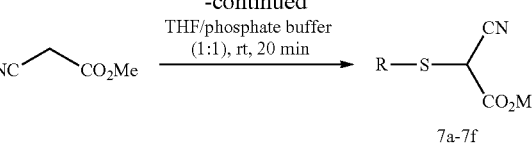

7a-7f

7a

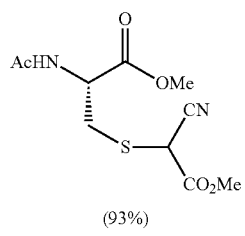

(93%)

7b

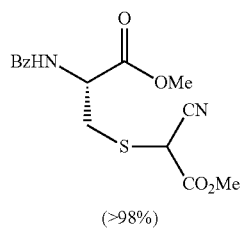

(>98%)

7c

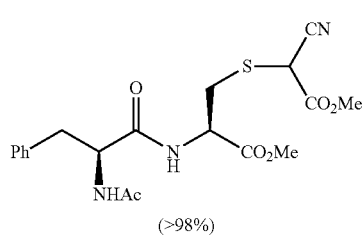

(>98%)

7d

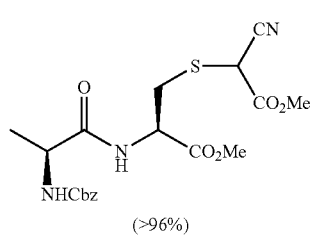

(>96%)

7e

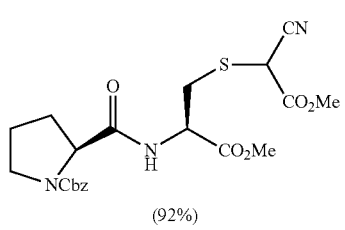

(92%)

7f

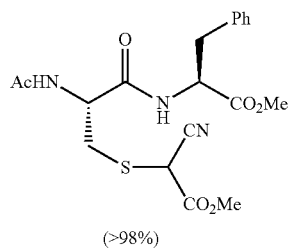

(>98%)

Given the dramatic structural changes in protein persulfide substrates, we tested whether MCA could effectively react with different R—S—S-BT substrates. The reaction scope was then studied using a series of cysteine-S—S-BT derivatives (Scheme 3). The reaction was found to be highly effective. In all cases the substitution products were afforded in good yields.

If MCA is used to specifically label protein persulfide derived R—S—S-BT moieties, it is critical to prove that MCA is inert towards common disulfides. We thus carried out several control experiments (Scheme S5 in Materials and Methods). The reactivity of MCA against Cys disulfide 8 was first examined. Under the tag-switch reaction conditions the corresponding product was not observed, even after several hours. The reactivity of MCA toward S-nitrosothiol 9, which represents another well-known thiol modification in proteins, was also checked. Again, no reaction was observed. Finally, a crossover experiment using both R—S—BT 10 (derived from thiols) and R—S—S-BT 4 (derived from persulfides) was tested. Only observed product 5f (from 4) was observed. The thiol-derived substrate 10 was unreactive and fully recovered. These results show that the proposed tag-switch method was selective for persulfides.

The results shown above demonstrate the chemistry foundation of the tag-switch method, which was then tested in protein samples. Glutathione peroxidase 3 (Gpx3), an established protein-S—SH model,[4] was used in this experiment. Freshly prepared Gpx3 persulfide was treated with MSBT-A, a water-soluble MSBT derivative,[7]

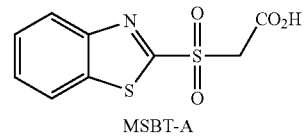

MSBT-A followed by the addition of cyanoacetate. The protein was then purified and analysed by liquid chromatography-mass spectrometry (LC-MS). As shown in FIG. 1B, cyanoacetate-labelled protein was clearly identified by MS. In the control (FIG. 1A, without MSBT-A), the cyanoacetate-labelled peak was not observed. An oxidative byproduct (P—S—SO$_3$H) was observed in both samples and this is common for Gpx3.[4]

The selectivity of tag-switch assay towards modified bovine serum albumin (BSA) samples was tested and confirmed A biotin-linked cyanoacetate (CN-biotin) was prepared and used in this study. Relatively stable sulfenic acid of bovine serum albumin (BSA-SOH) was prepared[10] and in reaction with glutathione[10,11] and H$_2$S corresponding glutathionylated and S-sulfhydrated derivatives were generated. None of BSA-SH, BSA-SOH, and BSA-SSG gave positive signals in the tag-switch assay. Only in the case of BSA-SSH could biotinylated product be detected.

These results showed that carbon-based nucleophiles such as cyanoacetate do not react with common disulfides in proteins, but do react selectivelwith highly chemically activated disulfide species. Taken together, these data show that the methods and reagents described herein are selective for the detection of protein S-sulfhydration.

Materials and Methods

Materials: Reagents and solvents were of the highest grade available. Reagent grade solvents were used for either chromatography or extraction without further purification before use. Dichloromethane (DCM) and tetrahydrofuran (THF) were directly used from a solvent purifier (Pure Solv, Innovative Technology, Inc.). Partially protected amino acids were purchased from Advanced ChemTech and used directly. 2-mercaptobenzothiazole, 2,2'-dibenzothiazolyl disulfide, malononitrile, methyl-2-cyanoacetate, and 1,3-cyclopentadione were purchased from TCI America and used directly. D-(+)-biotin was purchased from Acros and used directly.

Buffers was prepared with nano-pure water, stirred with Chelex-100 resins to remove traces of heavy metals and kept above the resins until used. Sodium sulfide ($Na_2S$) was purchased as anhydrous, opened and stored in glove box (<2 ppm $O_2$ and <1 ppm $H_2O$). 100 mM stock solutions of sodium sulfide were prepared as described previously.[14] $Fe^{3+}$(P) water-soluble porphyrin was a gift.).

Chromatography. The progress of the reactions was monitored by analytical thin layer chromatography (VWR, TLC 60 $F_{254}$ plates). Plates were visualized first with UV (254 nm) and then illuminated by CAM stain (2.5 g of ammonium molybdate tetrahydrate and 1 g of cerium ammonium sulfate in a solution of 10% sulfuric acid in water), $KMnO_4$ solution (1.5 g of $KMnO_4$, 10 g of $K_2CO_3$, and 1.25 mL of 10% NaOH), or ninhydrin solution (0.3% ninhydrin in a solution of 3% acetic acid in ethanol). Flash column chromatography was performed using silica gel (230-400 mesh). The solvent compositions for all separations are on a volume/volume (v/v) basis.

Reaction Between MSBT and Persulfides (the Preparation of 3):

To a solution of S-(4-trifluoromethylbenzothioacidic)-N—Ac-penicillamine-NHBu 1 (73.0 mg, 0.163 mmol) in dry THF (12 mL) was added MSBT (139 mg, 0.652 mmol) under argon atmosphere. Then a solution of benzyl amine (52.4 mg, 0.489 mmol) was added dropwise into the mixture at rt. The resulting mixture was stirred overnight and the solvent was removed under vacuum. The crude material was subjected to flash column chromatography (2% MeOH in DCM) to afford the desired product 3 as a brownish solid in 13% yield (9 mg). mp 167-168° C.; $^1$H NMR (300 MHz, $CDCl_3$) δ 8.04 (s, 1H), 7.78 (t, J=8.9 Hz, 2H), 7.42 (t, J=7.7 Hz, 1H), 7.32 (t, J=7.5 Hz, 1H), 6.90 (d, J=8.9 Hz, 1H), 4.87 (d, J=9.1 Hz, 1H), 3.43 (m, 1H), 3.27-3.09 (m, 1H), 2.02 (s, 3H), 1.52 (m, 5H), 1.39 (m, 5H), 0.89 (t, J=7.2 Hz, 3H); $^{13}$C NMR (75 MHz, $CDCl_3$) δ 170.4, 168.9, 153.9, 136.1, 126.6, 125.1, 121.9, 121.5, 58.7, 55.5, 39.7, 31.6, 31.2, 25.2, 23.6, 20.5, 14.0; IR (thin film, $cm^{-1}$) 3273, 3080, 2951, 2864, 1683, 1634, 1564, 1455, 1424, 1380, 1363, 1002, 749, 721; MS (ESI) m/z calcd for $C_{18}H_{25}N_3NaO_2S_3$ $[M+Na]^+$434.0. found 434.1.

Synthesis of R—S—S-BT Compounds

Preparation of Compound 4: To a solution of 2,2'-dibenzothiazoyl disulfide (523 mg, 1.57 mmol) in THF (50 mL) was added Ac-Cys-NHBn (330 mg, 1.30 mmol) in $CHCl_3$. The reaction mixture was stirred for 48 h at rt then concentrated. The resulting residue was subjected to flash column chromatography (2% MeOH in DCM) to give the desired product 4 as a solid (80% yield). mp 181-182° C.; $^1$H NMR (300 MHz, $CDCl_3$) δ 8.22 (t, J=5.2 Hz, 1H), 7.80-7.70 (m, 1H), 7.41 (dt, J=7.3, 3.1 Hz, 1H), 7.36-7.20 (m, 7H), 6.99 (d, J=7.5 Hz, 1H), 4.84 (td, J=7.7, 4.7 Hz, 1H), 4.68-4.37 (m, 2H), 3.51 (dd, J=14.2, 4.7 Hz, 1H), 3.11 (dd, J=14.2, 8.0 Hz, 1H), 1.98 (s, 3H); $^{13}$C NMR (75 MHz, $CD_3OD/CDCl_3$) δ 171.6, 169.9, 154.2, 137.6, 135.8, 128.7, 127.7, 127.6, 126.6, 125.1, 121.9, 121.4, 52.4, 43.7, 41.5, 22.6; FT-IR (thin film, $cm^{-1}$) 3293.1, 3268.6, 3060.2, 3023.4, 1618.5, 1544.2, 1454.3, 1421.6, 1004.6, 735.1; MS (ESI) m/z calcd for $C_{19}H_{19}N_3NaO_2S_3$ $[M+Na]^+$440.1. found 440.1.

Scheme S1. The reaction between MSBT and small molecule persulfides

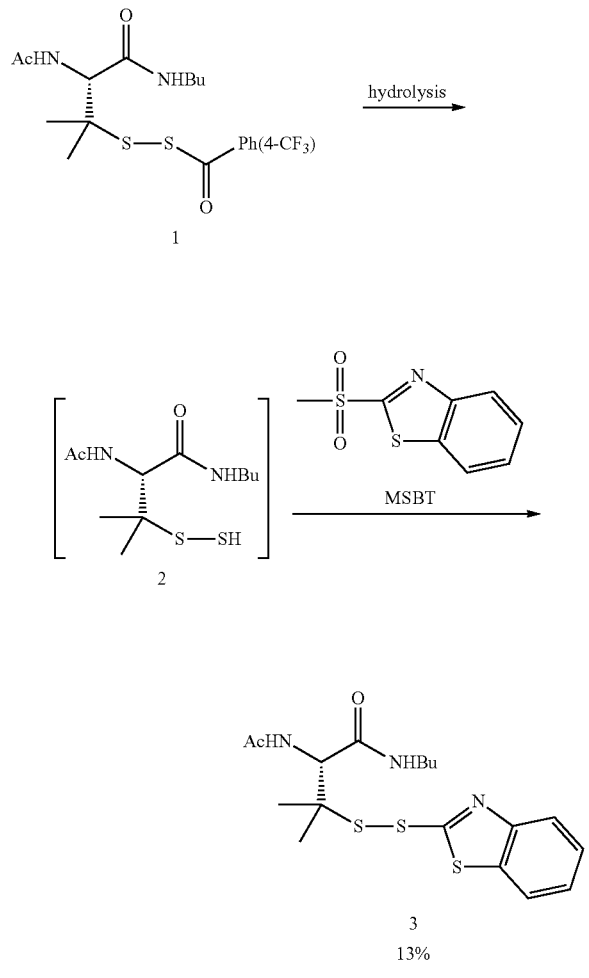

Scheme S2. Preparation of activated-disulfide model substrates

S1: $R_1$ = Ac, $R_2$ = OMe
S2: $R_1$ = Bz, $R_2$ = OMe
S3: $R_1$ = Ac-Phe, $R_2$ = OMe
S4: $R_1$ = Cbz-Ala, $R_2$ = OMe
S5: $R_1$ = Cbz-Pro, $R_2$ = OMe
S6: $R_1$ = Ac, $R_2$ = Phe-OMe

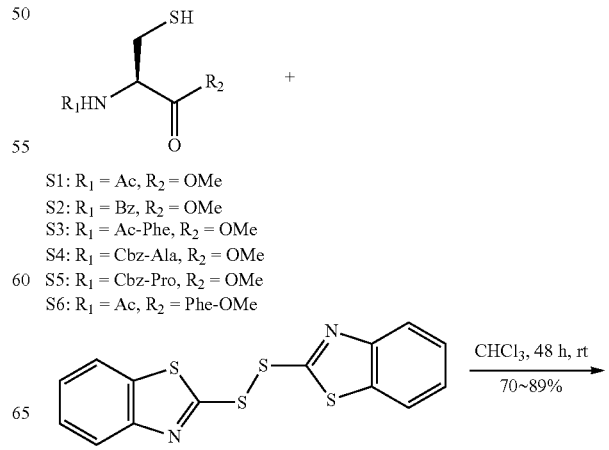

-continued

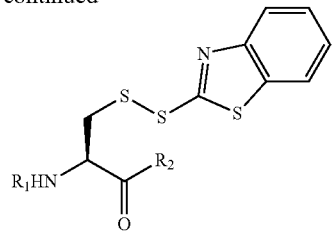

6a: R₁ = Ac, R₂ = OMe
6b: R₁ = Bz, R₂ = OMe
6c: R₁ = Ac-Phe, R₂ = OMe
6d: R₁ = Cbz-Ala, R₂ = OMe
6e: R₁ = Cbz-Pro, R₂ = OMe
6f: R₁ = Ac, R₂ = Phe-OMe

General Procedure for Compounds 6. To a solution of 2,2'-dibenzothiazoyl disulfide (1.2 mmol) in THF (50 mL) was added a solution of cysteine derivative (1 mmol) in CHCl₃. The reaction mixture was stirred for 48 h at room temperature and then concentrated. The resulting residue was subjected to flash column chromatography to give the desired product.

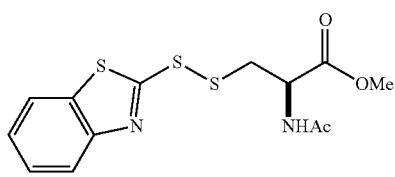

Compound 6a was obtained as a white solid (70% yield). mp 135-136° C.; $^1$H NMR (300 MHz, CDCl₃/CD₃OD) δ 8.36-8.17 (m, 2H), 7.94-7.83 (m, 1H), 7.85-7.75 (m, 1H), 5.31 (dd, J=7.4, 4.7 Hz, 1H), 4.18 (s, 3H), 3.92 (dd, J=14.1, 4.8 Hz, 1H), 3.80 (dd, J=14.1, 7.4 Hz, 1H), 2.47 (s, 3H); $^{13}$C NMR (75 MHz, CDCl₃/CD₃OD) δ 171.6, 170.6, 154.5, 135.6, 126.6, 125.0, 121.8, 121.3, 52.7, 51.9, 40.8, 22.2; FT-IR (thin film, cm$^{-1}$) 3288.9, 3061.0, 2920.6, 1745.2, 1733.0, 1649.3, 1545.3, 1467.8, 1337.3, 1241.4, 1002.8, 747.8; MS (ESI) m/z calcd for C₁₃H₁₄N₂NaO₃S₃ [M+Na]⁺ 365.0. found 365.0.

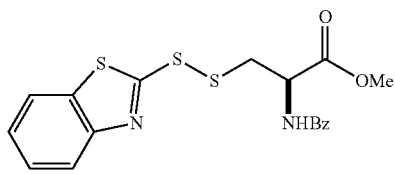

Compound 6b was obtained as a white solid (77% yield). mp 128-129° C.; $^1$H NMR (300 MHz, CDCl₃) δ 7.68-7.76 (m, 4H), 7.26-7.53 (m, 6H), 5.05-5.08 (m, 1H), 3.69 (s, 3H), 3.56 (d, J=4.8 Hz, 2H); $^{13}$C NMR (75 MHz, CDCl₃) δ 170.7, 167.4, 154.6, 136.1, 133.7, 132.2, 129.0, 128.9, 127.5, 126.7, 125.1, 122.4, 121.6, 53.2, 52.4, 41.7; FT-IR (thin film, cm$^{-1}$) 3361.3, 2954.4, 2926.1, 1741.0, 1641.1, 1516.1, 1462.0, 1210.0, 1003.9, 764.4; MS (ESI) m/z calcd for C₁₈H₁₆N₂NaO₃S₃ [M+Na]⁺ 427.0. found 427.1.

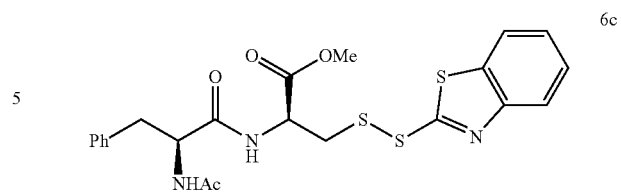

Compound 6c was obtained as a white solid (75% yield). mp 174-175° C.; $^1$H NMR (300 MHz, CDCl₃/CD₃OD) δ 8.47 (d, J=7.8 Hz, 2H), 8.24-7.96 (m, 3H), 7.86 (q, J=7.0 Hz, 4H), 5.44 (s, 1H), 5.32 (s, 1H), 4.35 (s, 3H), 4.17-4.02 (m, 1H), 3.93 (m, 1H), 3.73 (m, 1H), 3.58 (m, 1H), 2.58 (s, 3H); $^{13}$C NMR (75 MHz, CDCl₃/CD₃OD) δ 171.9, 171.8, 170.1, 154.6, 136.5, 129.2, 128.5, 126.8, 126.6, 125.0, 121.9, 121.4, 54.4, 54.3, 51.8, 40.7, 37.9, 37.8, 22.4, 22.3; FT-IR (thin film, cm$^{-1}$) 3301.2, 3260.4, 3068.3, 3027.6, 1732.1, 1670.6, 1642.2, 1527.8, 1425.7, 1000.7, 743.2; MS (ESI) m/z calcd for C₂₂H₂₃N₃NaO₄S₃ [M+Na]⁺512.1. found 512.2.

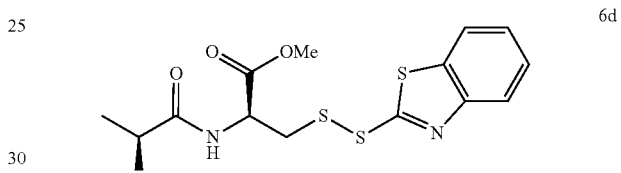

Compound 6d was obtained as a white solid (72% yield). mp 145-146° C.; $^1$H NMR (300 MHz, CDCl₃) δ 7.88 (d, J=8.1 Hz, 1H), 7.77 (d, J=7.9 Hz, 1H), 7.55-7.26 (m, 8H), 5.58 (d, J=7.5 Hz, 1H), 5.11 (s, 2H), 4.99-4.83 (m, 1H), 4.47-4.26 (m, 1H), 3.72 (s, 3H), 3.42 (m, 2H), 1.40 (d, J=7.1 Hz, 3H); $^{13}$C NMR (75 MHz, CDCl₃) δ 172.6, 170.9, 170.3, 156.2, 154.9, 136.4, 136.1, 128.8, 128.4, 128.3, 126.7, 125.2, 122.5, 121.5, 67.3, 53.2, 52.1, 50.7, 41.2, 18.8; FT-IR (thin film, cm$^{-1}$) 3269.0, 3093.1, 2987.5, 1736.2, 1646.3, 1683.1, 1531.9, 1258.1, 1000.7, 755.5; MS (ESI) m/z calcd for C₂₂H₂₃N₃NaO₅S₃ [M+Na]⁺ 528.1. found 528.1.

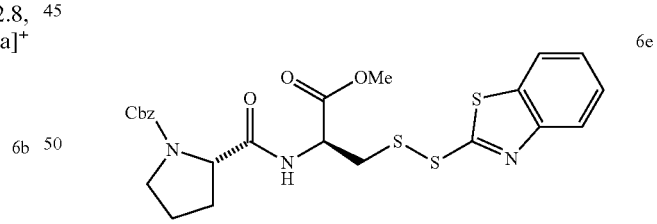

Compound 6e was obtained as a white solid (89% yield). mp 100-101° C.; The NMR spectra are reported for a dynamic equilibrium between two rotamers: $^1$H NMR (300 MHz, CDCl₃) δ 7.96-7.67 (m, 3H), 7.34 (m, 7H), 5.16 (s, 2H), 4.83 (m, 1H), 4.38 (m, 1H), 3.82-3.23 (m, 7H), 2.41-1.83 (m, 4H); $^{13}$C NMR (75 MHz, CDCl₃) δ 172.6, 171.9, 170.3, 156.1, 155.1, 136.6, 136.1, 128.7, 128.3, 128.2, 126.6, 125.1, 122.4, 121.5, 67.7, 61.0, 60.7, 53.1, 52.2, 51.7, 47.9, 47.3, 41.4, 31.4, 28.5, 24.8; FT-IR (thin film, cm$^{-1}$) 3329.9, 2974.3, 2945.7, 1740.3, 1703.4, 1695.3, 1654.5, 1519.6, 1417.5, 1352.1, 1205.0, 1111.0, 1090.6, 1000.7, 763.7; MS (ESI) m/z calcd for C₂₄H₂₅N₃NaO₅S₃ [M+Na]⁺ 554.1. found 554.1.

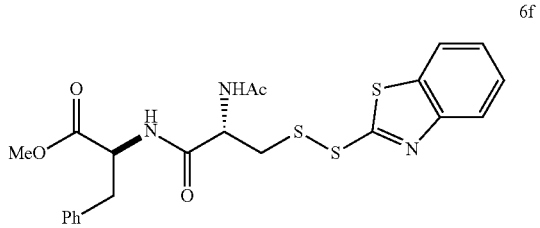

chromatography afforded the desired product 5f (as 1:1 diastereomers) in 98% as colorless sticky oil. $^1$H NMR (300 MHz, CDCl$_3$) δ 7.42 (s, 1H), 7.36-7.16 (m, 5H), 7.12-6.89 (m, 1H), 4.93-4.74 (m, 1H), 4.58 (d, J=8.3 Hz, 1H), 4.47-4.28 (m, 2H), 3.82 (s, 3H), 3.29-2.98 (m, 2H), 1.95 (s, 3H); $^{13}$C NMR (75 MHz, CDCl$_3$) δ 165.1, 164.7, 137.6, 128.9, 127.9, 127.8, 114.4, 114.2, 54.7, 54.6, 52.1, 52.1, 43.9, 36.2, 36.1, 34.9, 34.7, 23.2; FT-IR (thin film, cm$^{-1}$) 3280.8, 3072.4, 3035.6, 2953.9, 2925.3, 2247.0, 1746.5, 1635.7, 1523.7, 1458.3, 1433.8, 1368.4, 1311.2, 1229.5, 1025.2, 702.4; MS (ESI) m/z calcd for C$_{16}$H$_{19}$N$_3$NaO$_4$S [M+Na]$^+$ 372.1. found 372.1.

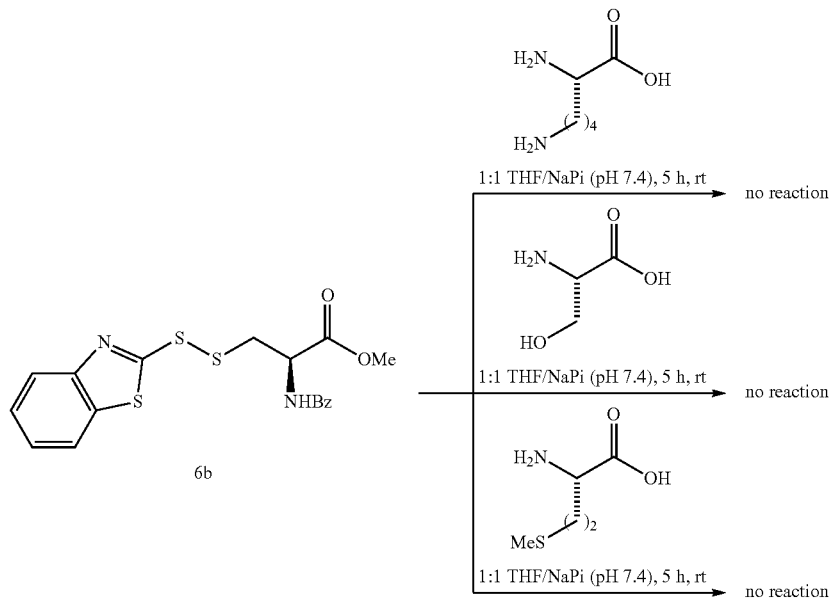

Scheme S3. Stability of R—S—S—BT toward potential biological nucleophiles

Compound 6f was obtained as a white solid (79% yield). mp 160-161° C.; $^1$H NMR (300 MHz, CDCl$_3$) δ 7.76 (d, J=8.0 Hz, 1H), 7.69 (d, J=7.8 Hz, 1H), 7.59 (d, J=7.7 Hz, 1H), 7.45-7.27 (m, 2H), 7.17 (m, 8.7 Hz, 6H), 5.00-4.75 (m, 2H), 3.68 (s, 3H), 3.43 (dd, J=14.1, 6.0 Hz, 1H), 3.19 (dd, J=14.3, 5.8 Hz, 2H), 3.07 (dd, J=13.9, 7.0 Hz, 1H), 1.92 (s, 3H); $^{13}$C NMR (75 MHz, CDCl$_3$) δ 171.6, 170.7, 169.8, 154.1, 136.4, 129.5, 128.8, 127.3, 126.7, 125.2, 122.2, 121.5, 54.0, 52.7, 52.6, 42.7, 37.8, 23.3; FT-IR (thin film, cm$^{-1}$) 3288.6, 3059.9, 2926.8, 1736.4, 1642.1, 1537.3, 1458.7, 1376.6, 1214.1, 1008.0, 754.7; MS (ESI) m/z calcd for C$_{22}$H$_{23}$N$_3$NaO$_4$S$_3$ [M+Na]$^+$ 512.1. found 512.1.

The Reaction Between 4 and MCA: To a round bottom flask containing compound 4 (93.7 mg, 0.224 mmol) was added 7 mL of THF. The solution was stirred for 5 min and then 7 mL of NaPi buffer (20 mM, pH 7.4) was added into the flask. The mixture was a homogeneous solution. MCA (2 eq, 44.5 mg, 0.449 mmol) was added at rt and the reaction was found to complete within 20 min (monitored by TLC). The aqueous mixture was quenched with 1N HCl (16 mL) and extracted with EtOAc (10 mL×3). The combined organic layers were dried and concentrated. Flash column General Procedure. To a solution of 6b (dissolved in 1:1 THF/NaPi (pH 7.4)) was added 5 equiv of corresponding nucleophiles (L-Lysine, L-Serine, and L-methionine). The reaction mixture was stirred for 5 h at room temperature. The reaction was monitored by TLC. We found that the starting material 6b was always fully recovered with no reactions.

Scheme S4. The reaction of R—S—S—BT substrates with carbon nucleophiles

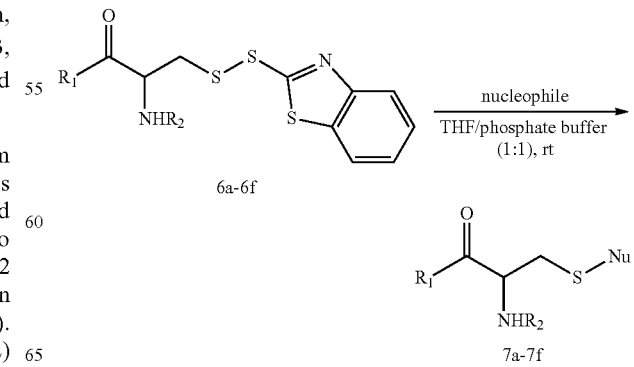

General Procedure. To a stirring solution of R—S—S-BT substrate (0.2 mmol) in THF (8 mL) and NaPi (20 mM, 8 mL) was added each carbon nucleophiles (0.4 mmol). The reaction mixture was then stirred for 20 min at room temperature and quenched with 1N HCl (16 mL). The solution was extracted with ethyl acetate (10 mL×3). The combined organic layers were washed with brine, dried over with anhydrous $MgSO_4$, and concentrated. The resulting residue was subjected to flash column chromatography to isolate the possible products or recovered starting materials.

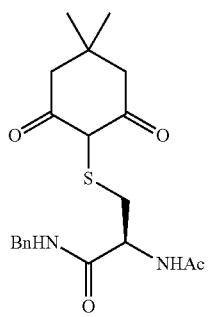

5b

Compound 5b: $^1$H NMR (300 MHz, $CDCl_3$) δ 8.30 (t, J=6.0 Hz, 1H), 7.76 (d, J=6.9 Hz, 1H), 7.35-7.20 (m, 5H), 4.44 (m, 4H), 3.12 (dd, J=13.6, 4.4 Hz, 1H), 2.43 (m, 5H), 2.02 (s, 3H), 1.09 (s, 6H); $^{13}$C NMR (75 MHz, $CDCl_3$) δ 191.8, 171.9, 171.4, 137.7, 128.6, 127.4, 127.4, 104.5, 53.1, 43.5, 37.7, 31.5, 29.7, 28.2, 22.6; FT-IR (thin film, cm$^{-1}$) 3268.5, 3066.1, 3029.5, 2952.4, 2923.4, 2854.0, 1645.1, 1543.0, 1475.5, 1369.9, 1264.3, 1144.9, 1025.5, 1009.9, 731.3; MS (ESI) 711/Z calcd for $C_{20}H_{26}N_2NaO_4S$ [M+Na]$^+$ 413.2. found 413.4.

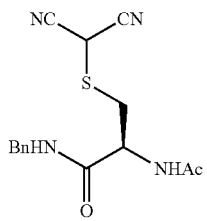

5e

Compound 5e: 1H NMR (300 MHz, DMSO-d6) δ 8.73 (t, J=6.0 Hz, 1H), 8.51 (d, J=8.4 Hz, 1H), 7.90 (s, 1H), 7.32-7.23 (m, 5H), 4.73 (m, 1H), 4.29-4.25 (m, 2H), 3.32-3.21 (m, 2H), 1.91-1.81 (m, 3H); $^{13}$C NMR (75 MHz, $CDCl_3$/MeOH-d4) δ 171.7, 169.4, 137.4, 128.8, 127.9, 127.7, 111, 110.9, 51.9, 43.9, 36.1, 29.9, 22.9; FT-IR (thin film, cm$^{-1}$) 3276.7, 3064.2, 3031.6, 2917.1, 2851.8, 2202.0, 2157.1, 2112.1, 1638.1, 1523.7, 1450.2, 1368.4, 1241.8, 698.3; MS (ESI) m/z calcd for $C_{15}H_{16}N_4O_2S$ [M-H]$^-$ 351.1. found 351.5.

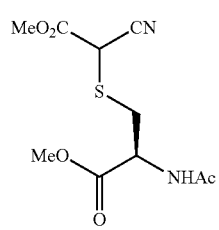

7a

Compound 7a was obtained as a thick oil (as 1:1 diastereomers, 93% yield). $^1$H NMR (300 MHz, $CDCl_3$) δ 6.38 (s, 1H), 4.90 (q, J=5.9 Hz, 1H), 4.43 (d, J=27.1 Hz, 1H), 3.87 (s, 3H), 3.81 (s, 3H), 3.53-3.31 (m, 1H), 3.32-3.15 (m, 1H), 2.07 (s, 3H); $^{13}$C NMR (75 MHz, $CDCl_3$) δ 170.7, 170.5, 164.6, 164.3, 114.1, 113.9, 54.6, 53.3, 51.8, 51.7, 36.1, 35.9, 34.7, 23.3; FT-IR (thin film, cm$^{-1}$) 3374.8, 3280.8, 2963.9, 2917.1, 2843.6, 2247.0, 1740.5, 1654.5, 1531.9, 1429.7, 1368.4, 1213.2, 1008.9; MS (ESI) m/z calcd for $C_{10}H_{14}N_2NaO_5S$ [M+Na]$^+$ 297.1. found 297.1.

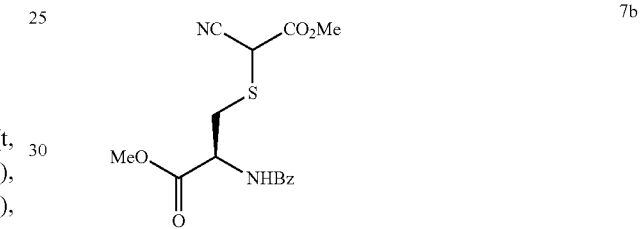

7b

Compound 7b was obtained as a thick oil (as 1:1 diastereomers, 99% yield). $^1$H NMR (300 MHz, $CDCl_3$) δ 7.91-7.74 (m, 2H), 7.59-7.36 (m, 3H), 7.18-7.02 (m, 1H), 5.08 (s, 1H), 4.59-4.35 (m, 1H), 3.82 (s, 6H), 3.54 (ddd, J=14.9, 10.0, 4.7 Hz, 1H), 3.34 (ddd, J=14.2, 9.2, 6.0 Hz, 1H); $^{13}$C NMR (75 MHz, $CDCl_3$) δ 170.8, 167.5, 164.6, 164.4, 133.4, 132.4, 128.9, 127.5, 114.0, 113.9, 54.6, 53.5, 53.4, 52.2, 52.2, 36.1, 35.9, 34.8, 34.6; FT-IR (thin film, cm$^{-1}$) 3329.9, 2953.9, 2921.2, 2855.8, 2242.9, 1740.8, 1642.2, 1519.6, 1486.9, 1429.7, 1213.2, 1017.0, 710.6; MS (ESI) m/z calcd for $C_{15}H_{16}N_2NaO_5S$ [M+Na]$^+$ 359.1. found 359.1.

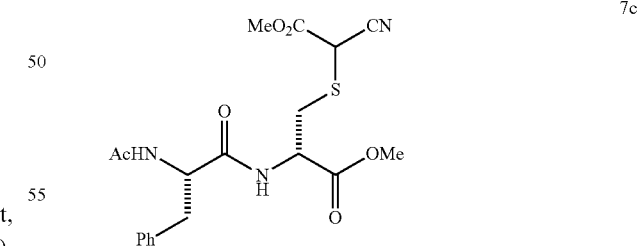

7c

Compound 7c was obtained as a yellowish solid (as 1:1 diastereomers, 99% yield). mp 113-114° C.; $^1$H NMR (300 MHz, $CDCl_3$) δ 7.37-7.04 (m, 6H), 6.53-6.30 (m, 1H), 4.87-4.65 (m, 2H), 4.55-4.28 (m, 1H), 3.77 (s, 3H), 3.67 (s, 3H), 3.36-2.97 (m, 4H), 1.89 (s, 3H); $^{13}$C NMR (75 MHz, $CDCl_3$) δ 171.7, 170.7, 170.1, 169.9, 164.7, 136.5, 129.6, 129.5, 128.8, 127.2, 114.3, 54.6, 54.6, 54.5, 53.3, 52.1, 52.0, 38.2, 36.2, 35.9, 34.6, 34.5, 23.3; FT-IR (thin film, cm$^{-1}$) 3287.4, 3034.3, 2910.5, 2251.4, 1746.0, 1730.8, 1664.2, 1545.0, 1431.1, 1367.4, 1298.2, 1032.3, 754.2; MS (ESI) m/z calcd for $C_{19}H_{23}N_3NaO_6S$ [M+Na]$^+$ 444.1. found 444.2.

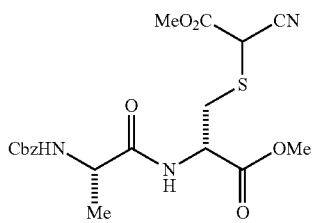

7d

Compound 7d was obtained as a thick oil (as 1:1 diastereomers, 96% yield): $^1$H NMR (300 MHz, CDCl$_3$) δ 7.61-6.98 (m, 6H), 5.60 (s, 1H), 5.10 (s, 2H), 4.87 (s, 1H), 4.67-4.42 (m, 1H), 4.32 (s, 1H), 3.81 (s, 3H), 3.76 (s, 3H), 3.47-3.11 (m, 2H), 1.38 (d, J=6.9 Hz, 3H); $^{13}$C NMR (75 MHz, CDCl$_3$) δ 172.9, 170.4, 170.3, 164.7, 164.7, 156.3, 136.4, 128.8, 128.4, 128.3, 114.4, 114.1, 67.3, 67.3, 54.6, 54.6, 53.3, 53.3, 52.0, 50.8, 36.2, 35.9, 34.6, 34.4, 18.6, 18.4; FT-IR spectra (thin film, cm$^{-1}$) 3313.5, 2953.9, 2921.2, 1851.8, 2247.0, 1740.3, 1738.5, 1670.8, 1515.6, 1429.7, 1319.4, 1209.1, 1017.0, 735.1, 702.4; MS (ESI) m/z calcd for $C_{19}H_{23}N_3NaO_7S$ [M+Na]$^+$ 460.1. found 460.2.

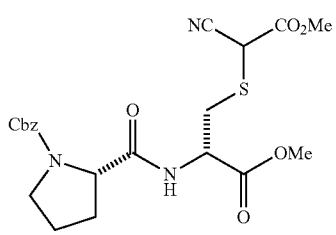

7e

Compound 7e was obtained as a thick oil (as 1:1 diastereomers, 92% yield): The NMR spectra are reported for a dynamic equilibrium between two rotamers: $^1$H NMR (300 MHz, CDCl$_3$) δ 7.79-7.11 (m, 6H), 5.13 (s, 2H), 4.98-4.52 (m, 2H), 4.49-4.23 (m, 1H), 3.93-3.65 (m, 6H), 3.60-3.27 (m, 3H), 3.13 (s, 1H), 2.29-1.87 (m, 4H); $^{13}$C NMR (75 MHz, CDCl$_3$) δ 172.8, 172.3, 170.3, 164.9, 164.7, 156.2, 155.2, 136.6, 128.7, 128.3, 128.2, 128.1, 114.2, 67.6, 61.0, 60.7, 54.5, 53.3, 53.22, 52.1, 51.9, 51.2, 51.1, 47.8, 47.2, 36.3, 35.7, 35.0, 34.7, 29.9, 28.9, 24.8, 23.9; FT-IR (thin film, cm$^{-1}$) 3317.1, 2962.1, 2947.5, 2851.8, 2242.9, 1748.5, 1679.0, 1519.6, 1454.3, 1433.8, 1405.2, 1352.1, 1209.1, 111.0, 739.2; MS (ESI) m/z calcd for $C_{21}H_{25}N_3NaO_7S$ [M+Na]$^+$ 486.1. found 486.1.

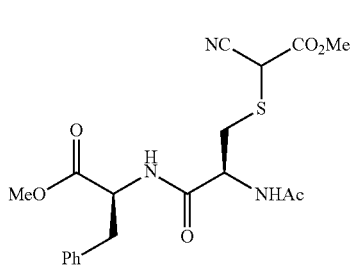

7f

Compound 7f was obtained as a thick oil (as 1:1 diastereomers, 99% yield): $^1$H NMR (300 MHz, CDCl$_3$) δ 7.33-7.15 (m, 4H), 7.18-7.02 (m, 2H), 6.88-6.65 (m, 1H), 4.89-4.68 (m, 2H), 4.61 (d, J=6.5 Hz, 1H), 3.82 (s, 3H), 3.70 (s, 3H), 3.26-2.93 (m, 4H), 1.95 (s, 3H); $^{13}$C NMR (75 MHz, CDCl$_3$) δ 171.6, 171.6, 170.9, 169.9, 165.2, 164.8, 135.9, 129.4, 128.8, 128.8, 127.4, 127.4, 114.6, 114.4, 54.7, 54.6, 53.9, 52.7, 51.9, 37.8, 37.8, 36.3, 36.3, 34.8, 34.5, 23.2; FT-IR (thin film, cm$^{-1}$) 3289.0, 3060.2, 3027.5, 2958.0, 2940.3, 2851.8, 2247.0, 1744.4, 1650.4, 1519.6, 1429.7, 1972.5, 1245.9, 1209.1, 1017.0, 743.2; MS (ESI) m/z calcd for $C_{19}H_{23}N_3NaO_6S$ [M+Na]$^+$ 444.1. found 444.2.

<u>Scheme S5. Control experiments</u>

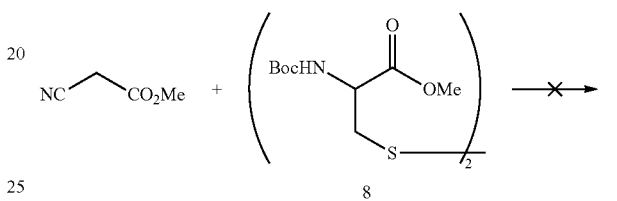

A

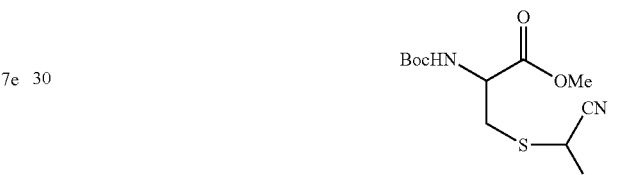

B

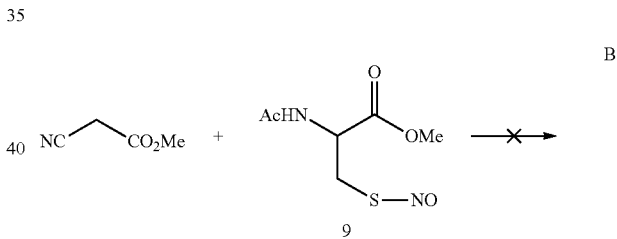

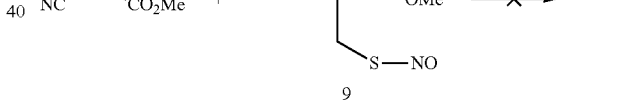

C

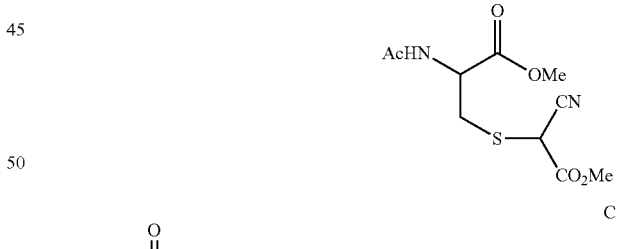

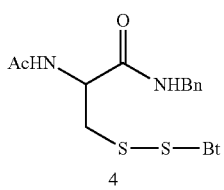

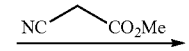

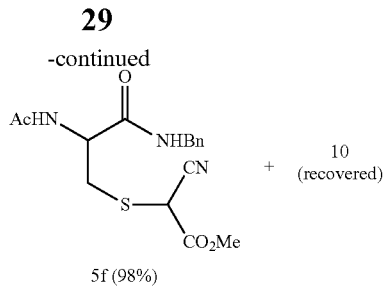

5f (98%)

+ 10 (recovered)

NMR (300 MHz, DMSO-d6) δ 7.96 (t, J=5.3 Hz, 1H), 6.43 (s, 1H), 6.37 (s, 1H), 4.30 (dd, J=7.7, 4.8 Hz, 1H), 4.11 (m, 3H), 3.97 (s, 2H), 3.36-3.23 (m, 2H), 3.16-3.03 (m, 1H), 2.82 (dd, J=12.4, 5.0 Hz, 1H), 2.57 (m, 1H), 2.06 (t, J=7.3 Hz, 2H), 1.68-1.37 (m, 4H), 1.29 (m, 2H); $^{13}$C NMR (75 MHz, DMSO-d6) δ 172.3, 164.3, 162.6, 114.9, 64.4, 60.9, 59.1, 55.3, 39.7, 37.1, 34.9, 28.1, 27.9, 25.0, 24.5. FT-IR (thin film, cm$^{-1}$) 3270.6, 3079.7, 2931.3, 2264.3, 2200.7, 1742.4, 1696.7, 1549.2, 1264.7, 1032.1, 726.8. MS (ESI) m/z, calcd for $C_{15}H_{22}N_4NaO_4S$ [M+Na]$^+$ 377.1. found 377.1.

Scheme S6.
Synthesis of biotinylated α-cyano ester (CN-biotin)

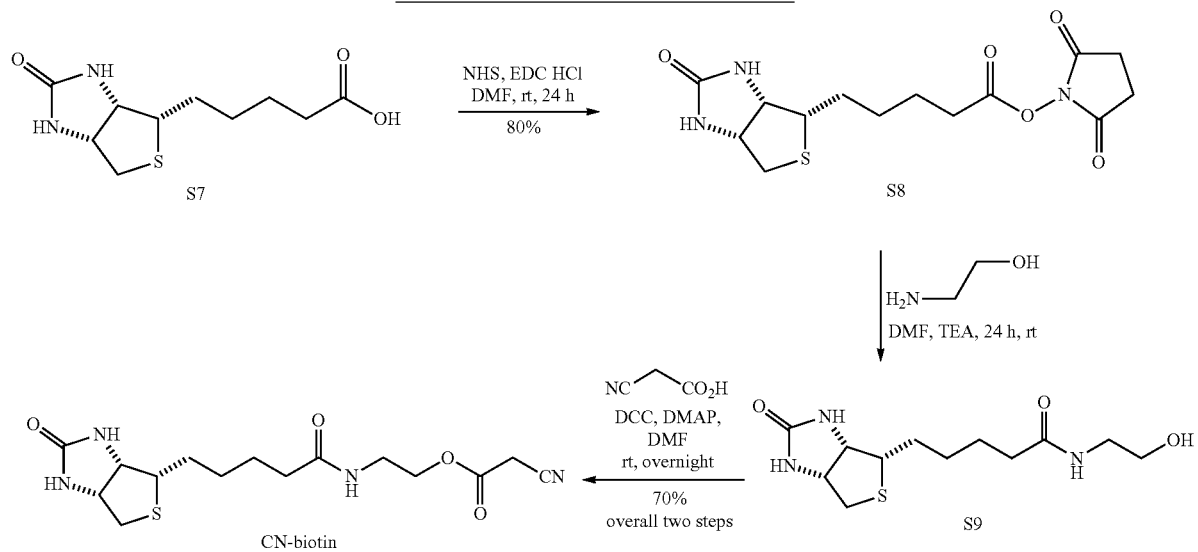

Compound S8. To a suspension of biotin S7 (4.06 mmol, 990 mg) in anhydrous DMF (60 mL) was added 1.1 equiv of N-hydroxysuccinimide (4.46 mmol, 514 mg). EDC.HCl (4.87 mmol, 933 mg) was then added and the reaction was stirred for 24 hours (at this time the solution turned clear). The solvent was then removed under reduced pressure to provide a white solid. The solid was washed thoroughly with anhydrous methanol, filtered and dried to provide S8 as a white solid (1.104 g, 80% yield). The product was used directly in the next step without any further purification.

Compound S9. To a solution of compound S8 (3.24 mmol, 1.104 g) in anhydrous DMF (66 mL) was added 2-aminoethanol (4.86 mmol, 0.29 mL) dropwise. Then, triethylamine (6.48 mmol, 0.9 mL) was added and the reaction mixture was stirred overnight. The solvent was removed under reduced pressure and the resulting residue was purified by flash column chromatography (gradient elution: 50:1 DCM/MeOH to 7:1 DCM/MeOH). The product S9 was used directly in the next step.

CN-Biotin. To a solution of compound S9 (3.24 mmol) in DMF (50 mL) was added cyanoacetic acid (3.89 mmol, 331 mg). DCC (4.2 mmol, 867 mg) was then added followed by DMAP (0.32 mmol, 40 mg). The reaction mixture was stirred overnight and the solvent was removed under reduced pressure to give the crude product. Flash column chromatography (gradient elution: 50:1 DCM/MeOH to 7:1 DCM/MeOH) afforded the final product as a white solid (804 mg). Yield: 70% for two steps. mp 132-134° C.; $^1$H Mass Analysis of Tag-Switch Assay with Gpx3-Persulfide: A freshly prepared Gpx3 protein persulfide solution[4] (20 μM final concentration) was incubated with (or without) MSBT-A (20 mM final concentration) respectively, followed by the addition of ethyl cyanoacetate (20 mM final concentration) at rt for 1 hour. The protein was then purified through a P-30 spin column. Sample aliquots were then generated and analyzed by LC-MS.

REFERENCES

[1] (a) L. Li, P. Rose, P. K. Moore, Annu. Rev. Pharmacol. Toxicol. 2011, 51, 169. b) O. Kabil, R. Banerjee, J. Biol. Chem. 2010, 285, 21903. (c) C. Szabo, Nature Rev. Drug Disc. 2007, 6, 917.

[2] (a) K. Abe, H. Kimura, J. Neurosci. 1996, 16, 1066. (b) W. Zhao, J. Zhang, Y. Lu, R. Wang, EMBO J. 2001, 20, 6008. (c) G. Yang, L. Wu, B. Jiang, W. Yang, J. Qi, K. Cao, Q. Meng, A. K. Mustafa, W. Mu, S. Zhang, S. H. Snyder, R. Wang, Science 2008, 322, 587. (d) A. K. Mustafa, G. Sikka, S. K. Gazi, J. Steppan, S. M. Jung, A. K. Bhunia, V. M. Barodka, F. K. Gazi, R. K. Barrow, R. Wang, L. M. Amzel, D. E. Berkowitz, S. H. Snyder, Circ. Res. 2011, 109, 1259. (e) J. W. Elrod, J. W. Calvert, J. Morrison, J. E. Doeller, D. W. Kraus, L. Tao, X. Jiao, R. Scalia, L. Kiss, C. Szabo, H. Kimura, C. W. Chow, D. J. Lefer, Proc. Natl. Acad. Sci. USA. 2007, 104, 15560.

[3] C. E. Paulsen, K. S. Carroll, Chem. Rev. 2013, 113, 4633.

[4] J. Pan, K. S. Carroll, ACS Chem. Biol. 2013, 8, 1110.

[5] (a) A. K. Mustafa, M. M. Gadalla, N. Sen, S. Kim, W. Mu, S. K. Gazi, R. K. Barrow, G. Yang, R. Wang, S. H. Snyder, Sci. Signaling. 2009, 2, ra72. (b) N. Sen, B. D. Paul, M. M. Gadalla, A. K. Mustafa, T. Sen, R. Xu, S. Kim, S. H. Snyder, Mol. Cell. 2012, 45, 13. (c) N. Krishnan, C. Fu, D. J. Pappin, N. K. Tonks, Sci. Signaling 2011, 4, ra86. (d) M. S. Vandiver, B. D. Paul, R. Xu, S. Karuppagounder, F. Rao, A. M. Snowman, H. S. Ko, Y. I. Lee, V. L. Dawson, T. M. Dawson, N. Sen, S. H. Snyder, Nat. Commun. 2013, 4, 1626. (e) B. D. Paul, S. H. Snyder, Nat. Rev. Mol. Cell Biol. 2012, 13, 499. (f) G. Yang, K. Zhao, Y. Ju, S. Mani, Q. Cao, S. Puukila, N. Khaper, L. Wu, R. Wang, Antioxid. Redox Signal. 2013, 18, 1906. (g) R. Greiner, Z. Pálinkás, K. Bäsell, D. Becher, H. Antelmann, P. Nagy, T. P. Dick. Antioxid. Redox Signal. 2013, doi:10.1089/ars.2012.5041.

[6] (a) Chapter 2 Thiol-Reactive Probes in The Molecular Probes Handbook: A guide to Fluorescent Probes and Labeling Technologies, 11th ed. I. Johnson and M. T. Z. Spence, editors. 2010, Life Technologies Corporation. 97-116. (b) G. T. Heimanson, Bioconjugate Techniques, 2nd ed., Elsiever Inc, 2008.

[7] D. Zhang, N. 0. Devarie-Baez, Q. Li, J. R. Lancaster, Jr., M. Xian, Org. Lett. 2012, 14, 3396.

[8] J. Pan, M. Xian, Chem. Commun. 2011, 47, 352.

[9] N. E. Heimer, L. Field, R. A. Neal, J. Org. Chem. 1981, 46, 1374.

[10] S. Carballal, R. Radi, M. C. Kirk, S. Barnes, B. A. Freeman, B. Alvarez. Biochemistry. 2003, 42, 9906.

All ranges described herein are intended to be inclusive, e.g. "from 2 to 40" includes 2 and 40.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of selectively detecting S-sulfhydration of cysteine residues in a protein, polypeptide or peptide, comprising
   i) exposing said protein, polypeptide or peptide to a first reagent that forms a covalent bond with —SH and —SSH groups, thereby forming disulfide adducts; then
   ii) exposing said protein, polypeptide or peptide to a second reagent comprising a nucleophile that selectively reacts with disulfide adducts formed from persulfide groups, wherein said second reagent further comprises a reporting molecule linked to said nucleophile via a linking molecule; and then
   iii) detecting said reporting molecule, wherein positive detection of said reporting molecule indicates that said cysteine residues of said protein, polypeptide or peptide were S-sulfhydrated.

2. The method of claim 1, wherein said nucleophile does not react with thioethers or disulfide bonds in proteins, polypeptides or peptides.

3. The method of claim 1, wherein said first reagent is i)

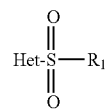

Formula I where Het is a heterocycle or heteroaryl and R1=—CR, —OR, —SR, or —NR, where R=an aryl or alkyl group;

or ii)

Het-R2    Formula II where Het is a heterocycle or heteroaryl and R2 is —F, —Cl, —Br, —I or —$N_2^+$.

4. The method of claim 3, wherein said heterocycle or heteroaryl is selected from the group consisting of

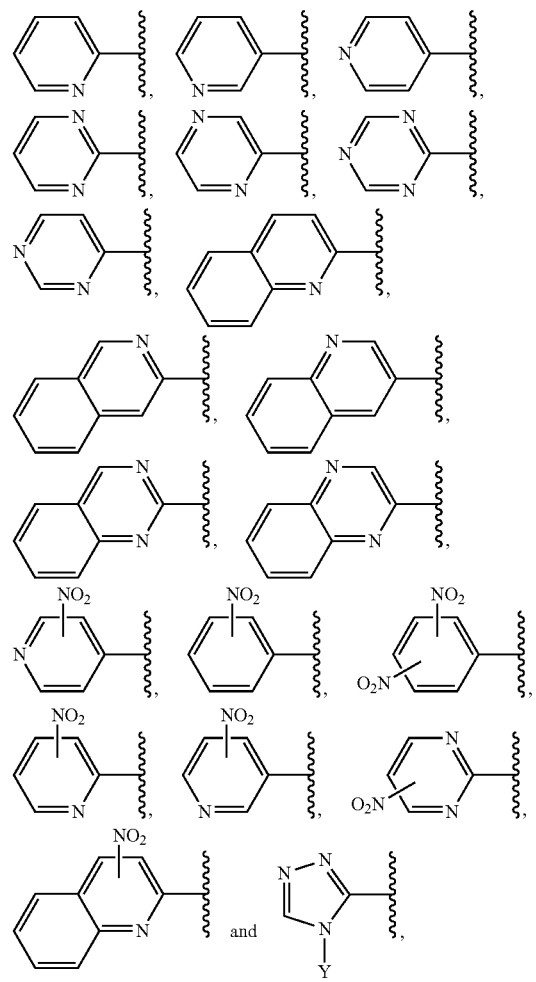

wherein Y is an aryl or alkyl group.

wherein Y is an aryl or alkyl group.

5. The method of claim 1, wherein said nucleophile is selected from the group consisting of

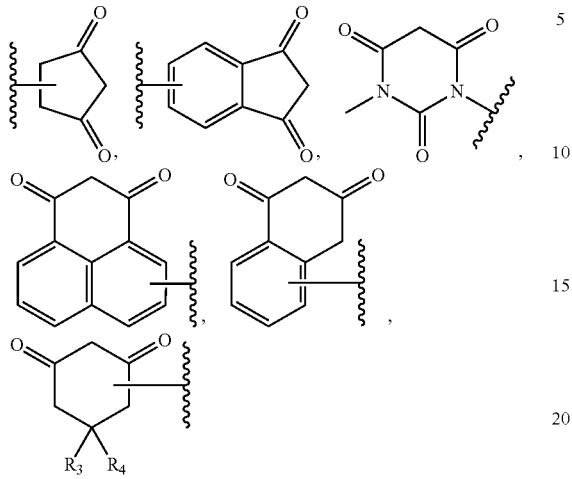

where R3 and R4 are independently selected from an aryl group and an alkyl group and may be the same or different;

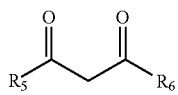

where R5 and R6 are independently selected from an aryl group and an alkyl group and may be the same or different; and

where R7 and R8 are independently selected from —NO$_2$, —CN, —SO$_2$R, —COOR or CONR and may be the same or different, and R=an aryl group or an alkyl group.

6. The method of claim 1, wherein said linking molecule is selected from the group consisting of

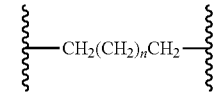

where n = 0 to 40

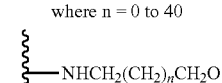

where n = 0 to 40,

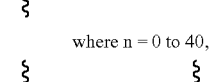

, and

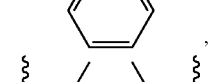

.

7. The method of claim 1, wherein said reporting molecule is selected from the group consisting of biotin, a fluorescent dye, a dansyl-based dye, a nitrobenzofurazan-based dye, rhodamine, a cyanine dye, a pyrene succinimidyl ester and a pyridyloxazole derivatives.

8. The method of claim 1, wherein said second reagent is associated with a solid support material, a resin, a dendrimer or a nanoparticle.

9. A kit comprising
a first reagent that forms a covalent bond with —SH and —SSH groups, thereby forming disulfide adducts; and
a second reagent comprising a nucleophile that selectively reacts with disulfide adducts formed from persulfide groups, wherein said second reagent further comprises a reporting molecule linked to said nucleophile via a linking molecule, and wherein said second reagent is immobilized on a substrate.

* * * * *